United States Patent [19]

Fohler

[11] Patent Number: 4,543,838
[45] Date of Patent: Oct. 1, 1985

[54] ARRANGEMENT FOR EXCHANGING MEASURING AND/OR SAMPLING PROBES

[75] Inventor: Johann Fohler, Puchenau, Austria

[73] Assignee: Voest-Alpine Aktiengesellschaft, Linz, Austria

[21] Appl. No.: 557,355

[22] Filed: Dec. 1, 1983

[30] Foreign Application Priority Data

Dec. 9, 1982 [AT] Austria .................................. 4475-82

[51] Int. Cl.⁴ .............................................. G01N 1/04
[52] U.S. Cl. .................................. 73/864.31; 73/432 R
[58] Field of Search ........... 73/61 LM, 432 B, 864.31, 73/864.59; 136/234; 266/99; 374/139, 140; 901/6, 45, 46, 47, 50

[56] References Cited

U.S. PATENT DOCUMENTS

| | | | |
|---|---|---|---|
| 3,948,093 | 4/1976 | Folchi et al. ........................ | 901/46 |
| 4,058,017 | 11/1977 | Tsujimoto et al. . | |
| 4,239,189 | 12/1980 | Scherff ................................. | 374/140 |

FOREIGN PATENT DOCUMENTS

| | | |
|---|---|---|
| 0092636 | 1/1983 | European Pat. Off. . |
| 2552270 | 6/1977 | Fed. Rep. of Germany . |
| 2753161 | 11/1977 | Fed. Rep. of Germany . |
| 2753077 | 6/1979 | Fed. Rep. of Germany . |
| 1493720 | 11/1977 | United Kingdom . |

*Primary Examiner*—S. Clement Swisher
*Attorney, Agent, or Firm*—Brumbaugh Graves Donohue & Raymond

[57] ABSTRACT

An arrangement for exchanging measuring and/or sampling probes capable of beig slipped on to a holding means arranged on the lower end of a lance, includes a grab clamping the probe and movable from an operation position below the lance into a position laterally therebeside. A centering means is provided above the grab being in the operation position to align the lance with the grab. In order that the grab will be placed always in the same operation position, the centering means includes two catch arms moveable from a resting position lateral of the holding means into a catch position fixing the holding means in alignment above the grab being in the working position.

3 Claims, 3 Drawing Figures

4,543,838

ARRANGEMENT FOR EXCHANGING MEASURING AND/OR SAMPLING PROBES

BACKGROUND OF THE INVENTION

The invention relates to an arrangement for exchanging measuring and/or sampling probes capable of being slipped on to a holding means arranged on the lower end of a lance, comprising a grab clamping the probe and movable from an operation position below the lance into a position laterally therebeside, a centering means being provided above the grab being in the operation position to align the lance with the grab.

In a prior arrangement of this kind (DE-B No. 27 53 161) tracing organs are employed as the centering means, which determine the position coordinates of the holding means and of the probe slipped on to the holding means, whereupon, in dependence on the position coordinates determined by the tracing organs, the grab is moved into these position coordinates. By this known arrangement it is possible to position the grab, or the probe, vertically below a warped lance or a bent holding means and to seize the probe slipped on to the holding means after having carried out a measurement in a metallurgical vessel. This known arrangement, however, requires complex means to determine the desired position of the grab. A further disadvantage is to be seen in that the arm of the arrangement carrying the grab must approach a new position at any grabbing procedure, according to the position of the lance, which calls for complex drives with the pertaining control means.

SUMMARY OF THE INVENTION

The invention aims at avoiding these disadvantages and difficulties and has as its object to provide an arrangement of the initially defined kind, which is as simple as possible in structural terms, with which the grab can be placed always in the same operation position so that special controlling and driving means to move the grab into different positions are not necessary.

This object is achieved according to the invention in that the centering means comprises two catch arms movable from a resting position lateral of the holding means into a catch position fixing the holding means in alignment above the grab which is in the operation position. According to the invention, it is not the grab that aligns with the lance or its probe holding means, but, to the contrary, the lance is aligned with the operation position of the grab, which is always the same.

According to a preferred embodiment, the catch arms are designed as superposed sickle-shaped arms and are pivotable from an opened resting position into a catch position embracing the holding means, i.e. by reducing the cross section of the space enclosed by the catch arms to the cross section of the holding means.

Advantageously, the centering means is mounted to an arm moving the grab.

BRIEF DESCRIPTION OF THE DRAWINGS

The invention will now be explained in more detail by way of one embodiment and with reference to the accompanying drawings, wherein.

DETAILED DESCRIPTION OF THE EXEMPLARY EMBODIMENT

Figure 1:
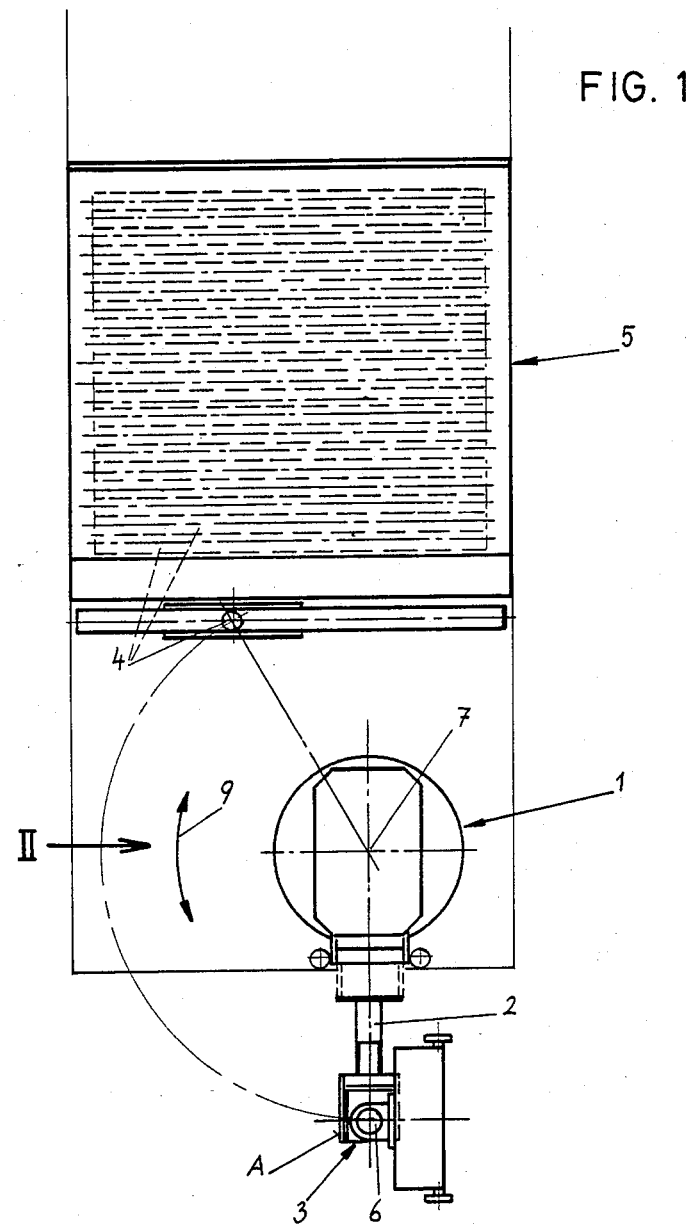
FIG. 1 is a top view of an arrangement for exchanging measuring and/or sampling probes positioned in a steel works.
Figure 2:
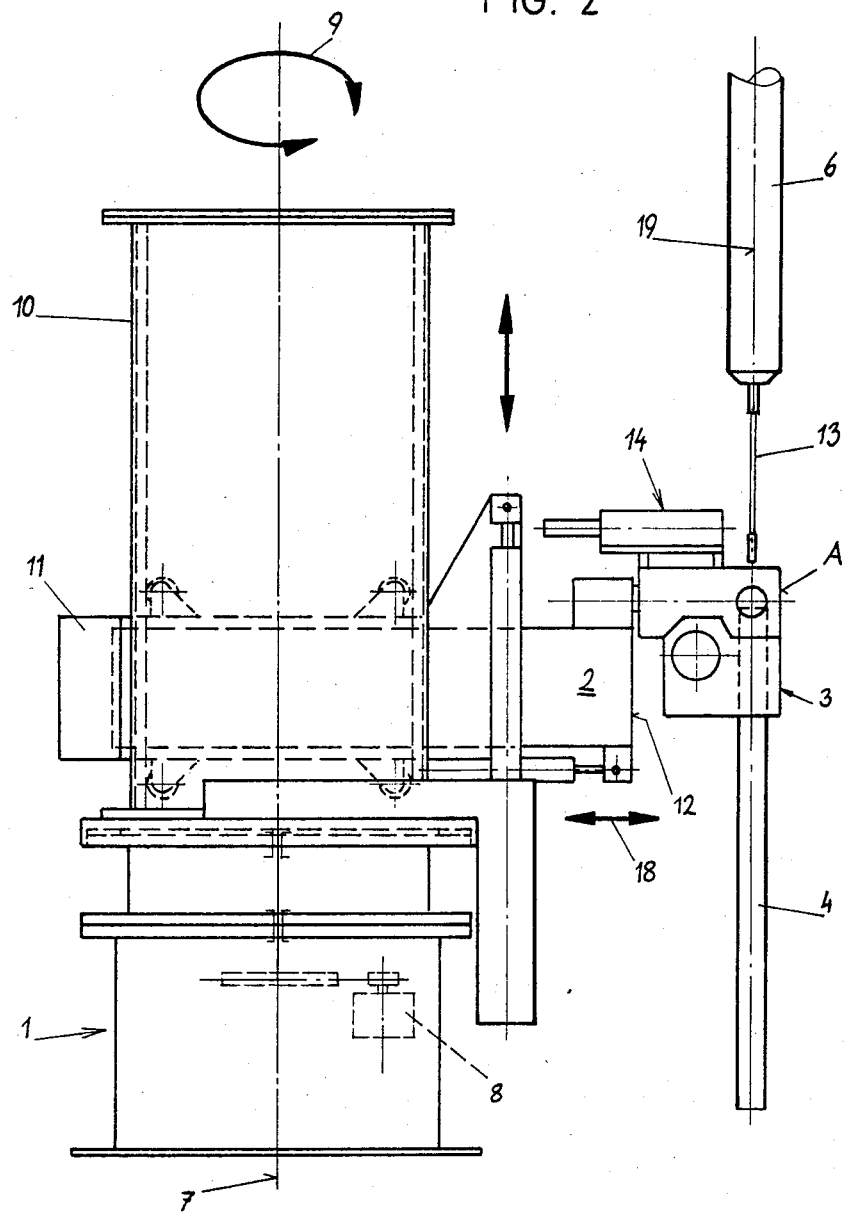
FIG. 2 is a view in the direction of the arrow II of FIG. 1.

A probe manipulator 1 comprises a grab 3 fastened to an arm 2, to accommodate a probe 4 from a magazine 5 and to transfer this probe 4 to a lance 6 or to remove the probe 4 from the lance 6. The manipulator comprises a column 10 (FIG. 2) that is rotatable about a vertical axis 7 in the direction of the double arrow 9 by means of a drive 8, a car 11 being mounted on the column so as to be displaceable in the vertical direction. This car 11 serves to accommodate the arm 2, which is displaceable in the horizontal direction and to whose free end 12 the grab 3 clamping the probe 4 is mounted. As is apparent from FIG. 1, the probe 4 can be taken from the magazine 5 by means of the grab 3 by pivoting about the axis 7 and can be placed into a position in alignment with below the lance 6. By lowering the lance 6, the probe is slipped on to the holding means mounted on the lance and designed as a holding rod 13. To remove the probe 4 from the lance 6, the probe 4 is clamped by the grab 3 and the lance 6 is pulled upwards after having carried out a measurement or sampling, the probe 4 thus being stripped off the holding rod 13, whereupon the probe 4 is taken to a delivery site by means of the grab 3.

As a result of an unbalanced temperature supply to the lance 6 within the metallurgical vessel, a distortion of the lance 6 may be caused so that, after a certain period of operation, the probe holder 13 provided on the lance 6 will no longer be in exact alignment above the probe 4 maintained in the slip-on position by means of the grab 3 pivoted in the operation position A. Furthermore, it may happen, during carrying out a measuring procedure or taking a sample, that the probe 4 is driven against stock not yet melted, whereby the holding rod 13 may be bent. A bending of the holding means also may be caused by contact of the probe 4 with slag parts floating on the molten stock.

In order to ensure the slipping on of the probe 4 to the holding rod in spite of such misalignment, a centering means 14 suitably is provided on the grab 3 above the same. As is apparent from FIG. 3, this centering means comprises two sickle-shaped catch arms 16 arranged symmetrically to the central axis 15 and pivotable about a pivot axis 17 intersecting the central axis 15, from a resting position B illustrated in FIG. 3 in full lines into a catch position C illustrated in FIG. 3 in broken lines.

The two superposed catch arms 16 are commonly pivoted, along pivot axis 17, on a guiding block 22, which is moveable in the horizontal direction 18 perpendicular to the lance axis 19 along guiding columns 20 fastened to a sled 21, the sled 21 is also displaceable horizontally and normal to the axis 19 of the lance 6. Guides 24 arranged in a frame 23 and extending parallel to the guiding columns 20 serve to horizontally guide the sled 21.

A linear drive, which is designed as a pressure medium cylinder 25, is hinged to the frame 23 on the one hand and to the sled 21—by its piston rod 26—on the other hand. The catch arms 16 are connected with the sled 21 by means of straps 27 hinged to them at a distance from the pivot axis 17.

Between the sled 21 and the guiding block 22 a helical spring 28, under tension, is provided. A pin 29 extending parallel to the guides 24 and to the guiding columns 20 serves to maintain the spring 28 in position.

The arrangement functions in the following manner:

If the linear drive 25 is actuated, the sled 21, which initially is in the resting position, shown in solid line, is displaced along the guides 24 in the direction towards the lance 6, the guiding block 22, which is held at a distance from the sled 21 by the helical spring 28, thus being synchronously displaced together therewith. Thus the catch arms 16, in the opened state, are moved into a position above the grab 3.

The movement of the guiding block 22 is stopped by a stop (not illustrated) as soon as it has reached the front end of the frame 23. The sled 21, however, moves on under the action of the linear drive 25 so that the distance between the sled 21 and the guiding block 22 will be reduced upon compression of the helical spring 28. As a result of the relative movement taking place between the sled 21 and the guiding block 22, the catch arms 16 are moved into the catch position C by means of the straps 27.

Figure 3:
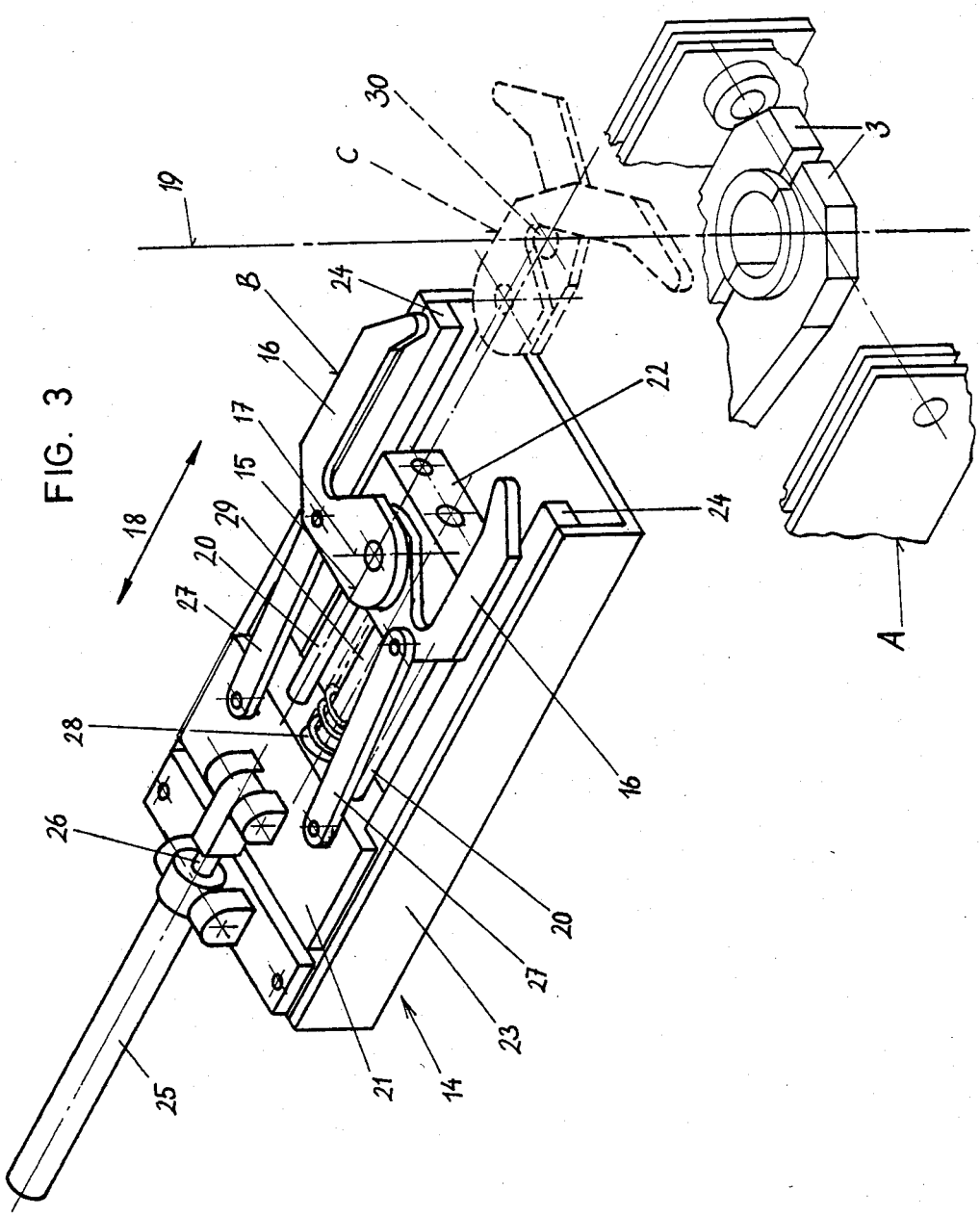
FIG. 3 is an isometric view of a centering means.

As can be seen from FIG. 3, the shape of the catch arms 16 is such that the overlapping catch arms 16, in the catch position C, enclose a free space 30 adapted to the cross section of the part to be caught. According to the embodiment illustrated, this free space is approximately circular and, with respect to its diameter, corresponds to the diameter of the holding rod 13 provided on the lance 6 for the probes 4.

During slipping on of the probe 4 to the holding rod 13, the linear drive 25 is actuated from a certain height of the slip-on movement in order to start the retraction movement of the catch arms 16. Therein, at first only the sled 21 moves along the guides 24 away from the axis 19 of the lance 6, while the guiding block, due to the tension force of the spring 28, initially remains in its foremost position. During this backward movement of the sled 21, the catch arms 16 are being opened. If the end of the spring range has been reached by the sled 21, the sled 21 and the guiding block 22 synchronously move back as far as to the stroke end of the linear drive 25, whereby the catch arms 16 are retracted into position B and thus do no longer restrict the space above the grab.

What I claim is:

1. In an arrangement for exchanging measuring and-/or sampling probes, in which said probes are slippable on and removable from a holding means on the lower end of a lance, said arrangement including a grab adapted to clamp said probes and movable between an operation position below said lance and a position laterally displaced therefrom, centering means arranged above said grab for aligning said lance with said grab, said centering means comprising
   a pair of catch arms adapted to engage and constrain movement of said holding means, and
   means for moving said pair of catch arms from a resting position laterally displaced from said holding means to a catch position in which said catch arms engage and maintain said holding means in alignment with and above said grab when said grab is in the operation position.
2. An arrangement as set forth in claim 1, wherein said grab is mounted on a movable arm and said centering means also is mounted an said arm for movement with said grab.
3. In an arrangement for exchanging measuring and-/or sampling probes, in which said probes are slippable on and removable from a holding means on the lower end of a lance, said arrangement including a grab adapted to clamp said probes and movable between an operation position below said lance and a position laterally displaced therefrom, centering means arranged above said grab for aligning said lance with said grab, said centering means comprising
   a pair of catch arms movable from a resting position lateral of said holding means into a catch position fixing said holding means in alignment above said grab when said grab is in the operation position,
   said catch arms being sickle-shaped arms arranged above each other and pivotable from an opened resting position into a catch position engaging said holding means, wherein pivoting of said arms into said catch position reduced the cross-section of the space enclosed by said catch arms to the cross-section of said holding means.

* * * * *